United States Patent
Loubinoux et al.

[11] Patent Number: 6,109,066
[45] Date of Patent: Aug. 29, 2000

[54] DEVICE FOR MANUFACTURING A COMPOSITE YARN

[75] Inventors: Dominique Loubinoux, La Terrasse; Daniel Richard, Sainte-Helene-du-Lac, both of France

[73] Assignee: Vetrotex France S.A., Chambery, France

[21] Appl. No.: 09/029,606

[22] PCT Filed: Jul. 3, 1997

[86] PCT No.: PCT/FR97/01184

§ 371 Date: Jun. 17, 1998

§ 102(e) Date: Jun. 17, 1998

[87] PCT Pub. No.: WO98/01751

PCT Pub. Date: Jan. 15, 1998

[30] Foreign Application Priority Data

Jul. 10, 1996 [FR] France ................................. 96/08592

[51] Int. Cl.$^7$ .................................................. C03B 37/07
[52] U.S. Cl. .................. 65/485; 65/986; 65/529; 65/539; 264/211.12; 264/412
[58] Field of Search ............... 65/442, 529, 485, 65/486, 539; 264/211.12, 176.1, 408, 412, 480, 464

[56] References Cited

U.S. PATENT DOCUMENTS

| | | | |
|---|---|---|---|
| 2,930,102 | 3/1960 | Hitchin | 364/408 |
| 3,844,497 | 10/1974 | Harrill | 65/486 |
| 4,230,284 | 10/1980 | Cunningham | 65/486 |
| 4,342,579 | 8/1982 | Sanders | 65/485 |
| 4,492,662 | 1/1985 | Larrive . | |
| 5,156,347 | 10/1992 | Gay . | |
| 5,425,796 | 6/1995 | Loubinoux | 65/442 |
| 5,454,846 | 10/1995 | Roncato | 65/442 |
| 5,582,843 | 12/1996 | Sellars | 264/408 |

*Primary Examiner*—John Hoffmann
*Attorney, Agent, or Firm*—Oblon, Spivak, McClelland, Maier & Neustadt, P.C.

[57] ABSTRACT

The subject of the invention is a device for manufacturing a composite yarn formed by the combination of continuous glass filaments and continuous filaments of a thermoplastic organic substance, comprising, on the one hand, at least one bushing which is fed with glass, the lower face of which is provided with a multiplicity of orifices from which a multiplicity of glass filaments is drawn, and is associated with a coating device and, on the other hand, at least one extrusion head fed with a molten thermoplastic organic substance, the lower face of which is provided with a multiplicity of orifices from which a multiplicity of organic filaments is drawn, the said head being associated with a drawing device comprising at least two drums and with a venturi device which projects the organic filaments into the sheet formed by the glass filaments, and means, common to the bushing and to the extrusion head, which enable the composite yarn to be assembled and drawn, for example by a winding device such as a bobbin winder provided with spindles, in which an optical device for detecting the sheet of thermoplastic filaments running through a defined region is arranged between the drum-type drawing device and the venturi device, the said optical device being connected to a circuit which controls the speed of rotation of at least one of the drums.

20 Claims, 3 Drawing Sheets

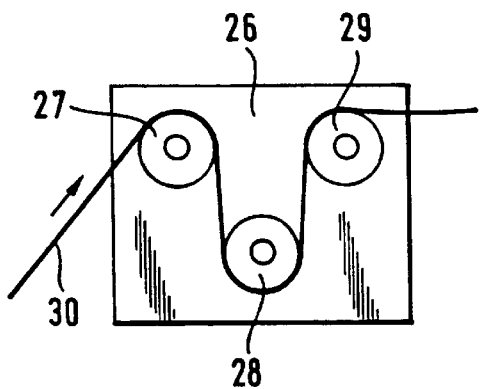
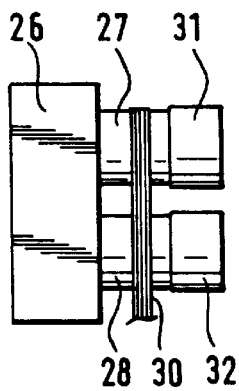
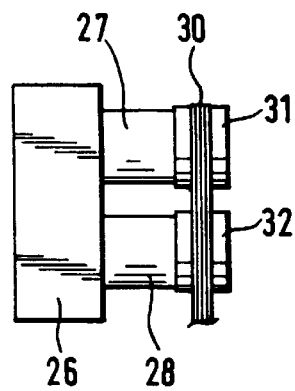
Fig. 2A  Fig. 2B  Fig. 2C
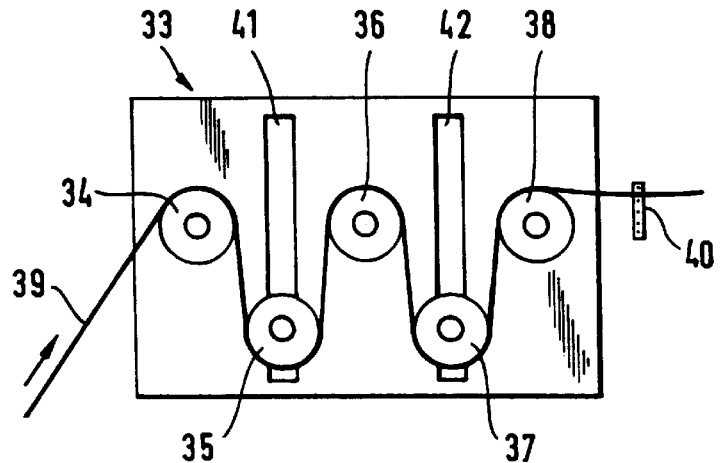
Fig. 3A
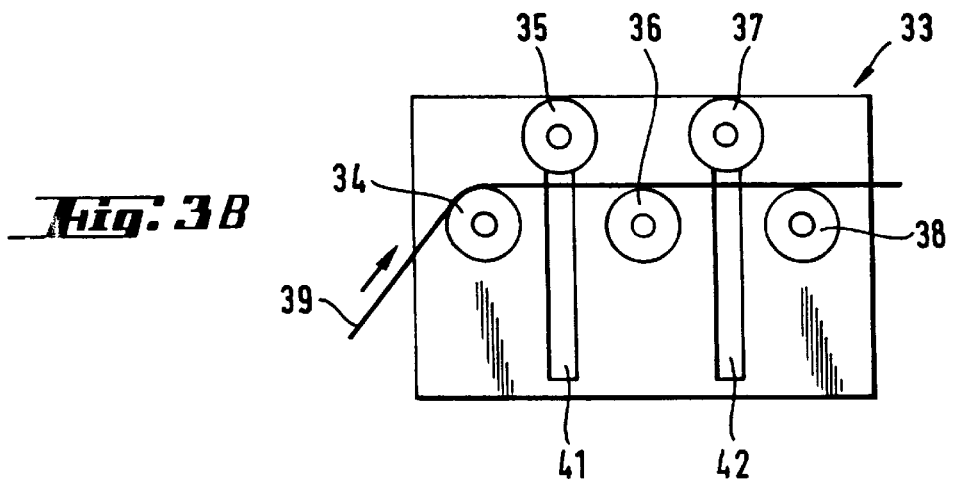
Fig. 3B

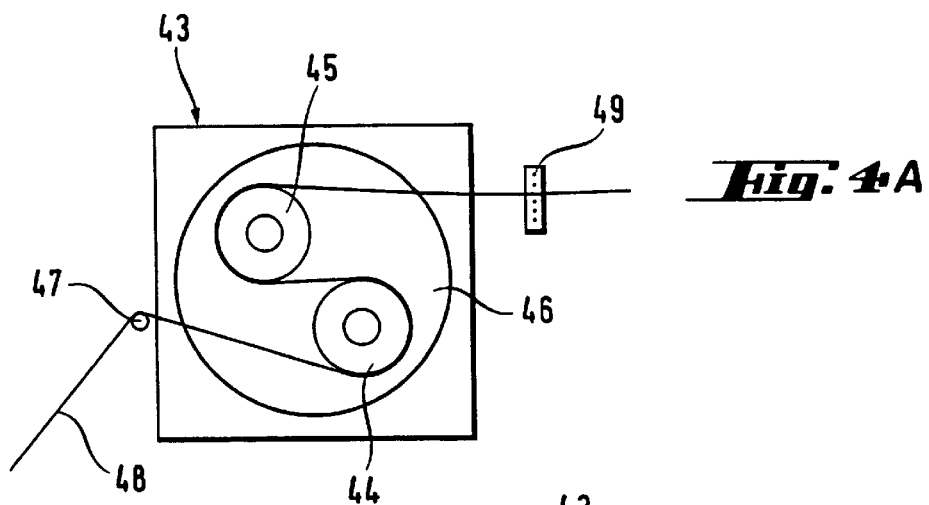
Fig. 4A
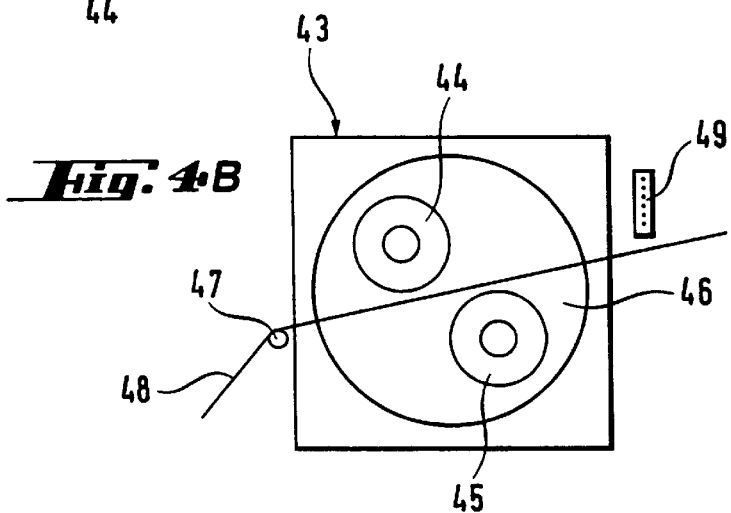
Fig. 4B
Fig. 4C
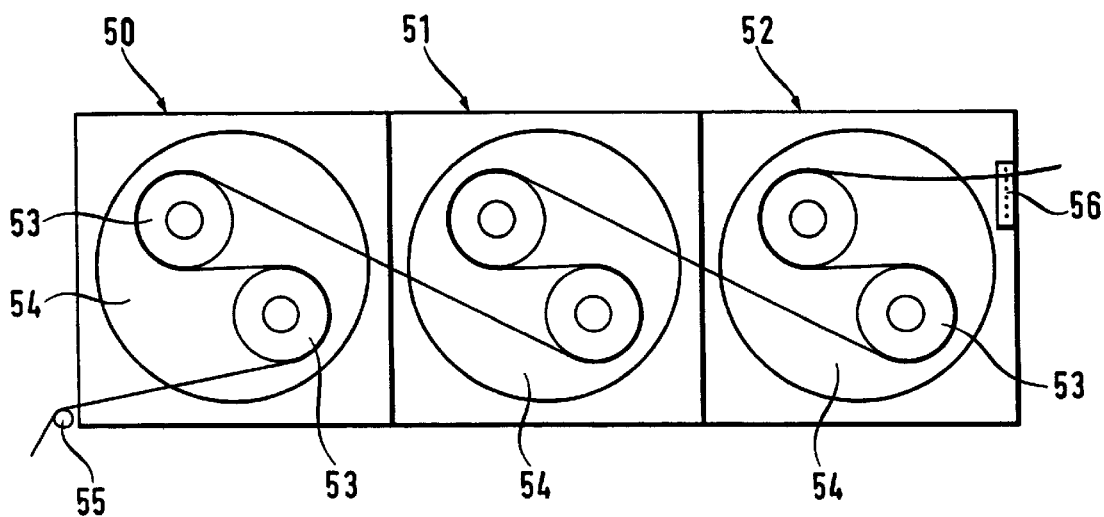

DEVICE FOR MANUFACTURING A COMPOSITE YARN

BACKGROUND OF THE INVENTION

1. Field of the Invention

The present invention relates to a device for manufacturing a composite yarn formed by the combination of a multiplicity of continuous glass filaments and of thermoplastic organic filaments.

More specifically, the invention relates to a device comprising at least one bushing fed with glass, from which is drawn a multiplicity of continuous glass filaments, and at least one extrusion head fed with a thermoplastic organic substance, from which is also drawn a multiplicity of continuous organic filaments. These organic filaments are drawn and projected by means of a venturi device into the sheet of glass filaments being drawn, all the said filaments then being gathered into the form of a composite yarn.

2. Discussion of the Background

Such an installation is described, for example, in Patent Application FR-A-2,698,038.

In the context of the invention described in that application, the thermoplastic filaments are drawn, separately from the glass filaments, by means of drums whose speed of rotation is controlled so as to give the sheet of thermoplastic filaments a speed greater than the drawing speed of the glass filaments. The sheet of thermoplastic filaments, optionally guided, passes through a venturi device which orients and projects the said sheet into the sheet of glass filaments being drawn. The device, which maintains the speed given to the thermoplastic filaments by the drawing drums, only projects the said filaments into the sheet of glass filaments, keeping them individualized. The difference thus created between the drawing speeds of the two categories of filaments has the effect of compensating for the shrinkage of the thermoplastic filaments which occurs before the composite yarn is wound. It is thus possible to obtain bobbins of composite yarn in which all the filaments of which it is composed have the same length. The appearance of a discrepancy between the desired speeds for the filaments, even when it is small, can result in a defect in the product obtained or can result in an incorrect operation of the installation.

This is the case when a discrepancy occurs between the speed given to the thermoplastic filaments by the drawing drums and the speed of the said filaments when they come into contact with the glass filaments.

SUMMARY OF THE INVENTION

The subject of the present invention is a device for manufacturing a composite yarn, in which the speed of rotation of the drums and the speed of the thermoplastic filaments when they come into contact with the glass filaments are automatically synchronized.

The subject of the present invention is a device for manufacturing a composite yarn in which the automatic synchronization of the speeds in question can be effected whatever the nature of the thermoplastic employed and the speed adopted for drawing the thermoplastic filaments.

These objectives are achieved by a device for manufacturing a composite yarn formed by the combination of continuous glass filaments and continuous filaments of a thermoplastic organic substance, comprising, on the one hand, at least one bushing which is fed with glass, the lower face of which is provided with a multiplicity of orifices from which a multiplicity of glass filaments is drawn, and is associated with a coating device and, on the other hand, at least one extrusion head fed with a molten thermoplastic organic substance, the lower face of which is provided with a multiplicity of orifices from which a multiplicity of organic filaments is drawn, the said head being associated with a drawing device comprising at least two drums and with a venturi device which projects the organic filaments into the sheet formed by the glass filaments, and means, common to the bushing and to the extrusion head, which enable the composite yarn to be assembled and drawn, for example by a winding device such as a bobbin winder provided with spindles, in which an optical device for detecting the sheet of thermoplastic filaments running through a defined region is arranged between the drum-type drawing device and the venturi device, the said optical device being connected to a circuit which controls the speed of rotation of at least one of the drums.

This detection device comprises at least two detectors placed on a support at different heights which define the limits of a region through which the said sheet can move during the operation of drawing the thermoplastic filaments.

In this detection device, the detectors may be arranged on just one side of the sheet of filaments. Each detector comprises an emitter and a receiver, the former emitting a light beam towards the sheet and the latter receiving at least some of the light reflected by the filaments which encounter the said beam.

The detectors may also consist of emitters and of receivers which are arranged on each side of the sheet; each emitter then acts together with a receiver which receives or does not receive the light beam which it emits, depending on the absence or presence of filaments in the region through which the said beam passes.

The emitters used preferably emit a light beam consisting of regular pulses. Recognition of these pulses by the receivers makes it possible to reduce, or even eliminate, the spurious signals, coming from light sources other than the said emitters, likely to be recorded by the said sensors.

A signal corresponding to the recognition by each receiver of the presence or absence of filaments in its field of examination is transmitted to an amplifier which sends a binary signal to a controller. This controller has an analogue or digital control output which is connected to the speed-setting input of the control device for the motor or motors which rotate the drawing drums.

Depending on the position of the sheet of filaments between the last drawing drum and the venturi device, in which position it is under a greater or lesser tension, the detectors periodically transmit a series of binary signals to the controller via the amplifier.

Depending on the nature of these signals, the controller increases or decreases the speed of the motor or motors rotating the drawing drums. In order to avoid uninterrupted alternations of acceleration and deceleration, time constants may be introduced into the control circuit, the increases and decreases in the speed of the motor or motors being precisely regulated. An actual loop for regulating the tension in the sheet is thus set up.

BRIEF DESCRIPTION OF THE DRAWINGS

The detailed description hereinbelow will enable the advantages of the present invention to be more clearly understood. This description is illustrated by figures in which:

FIGS. 2A, 2B, 2C show diagrammatically front and side view of a first embodiment of the device for drawing the sheet of thermoplastic filaments, FIGS. 3A and 3B show diagrammatically a second embodiment of the device for drawing the sheet of thermoplastic filaments, and FIGS. 4A, 4B and 4C show diagrammatically a third embodiment of the device for drawing the sheet of thermoplastic filaments.

DISCUSSION OF THE PREFERRED EMBODIMENTS

Figure 1:
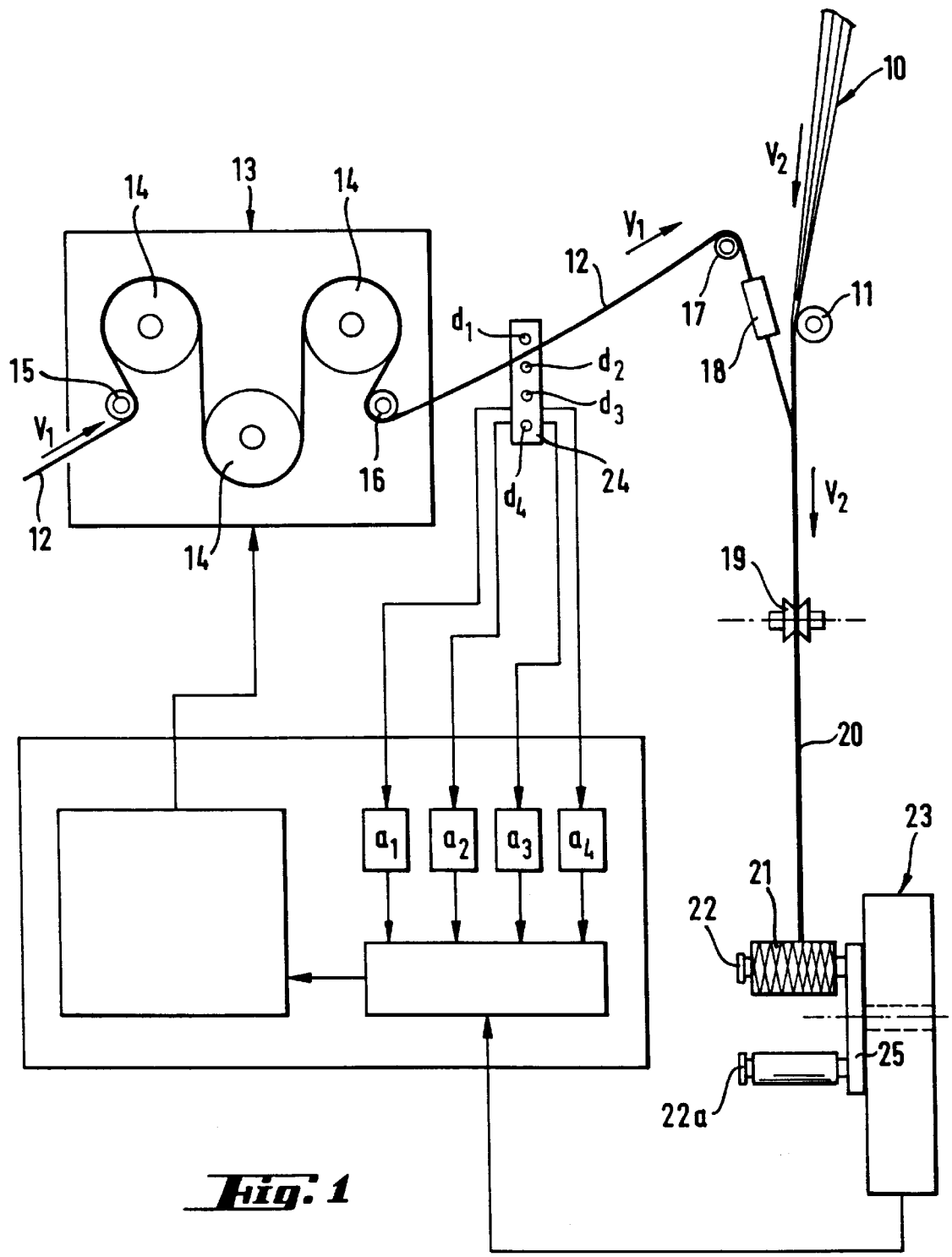
FIG. 1 shows a diagrammatic view of a device for detecting the sheet of thermoplastic filaments and of the circuit for controlling their drawing speed in the context of an installation for manufacturing a composite yarn.

The detection device shown in FIG. 1 is inserted into an installation for manufacturing a composite yarn formed by the combination of continuous glass filaments and continuous thermoplastic filaments.

This installation comprises a bushing fed with glass, the lower face of which is provided with a multiplicity of orifices from which is drawn a multiplicity of continuous filaments in the form of at least one bundle 10. This bundle passes over a coating device, shown symbolically by the roller 11, which is fed with primer or with size. On coming into contact with it, the filaments of the said bundle of the sheet 10 are covered with this primer or with this size.

This installation also comprises an extrusion head, not shown, from which is extruded a multiplicity of continuous filaments of a thermoplastic organic substance, such as polypropylene. These filaments are drawn into the form of a sheet 12 by means of a device 13 equipped with three motor-driven drums 14 before and after which are deflection rollers 15 and 16 which enable the arc of contact of the said sheet with the said drums to be increased. Next, the sheet 12 passes over a guide roller 17 before passing through a venturi device 18 which projects it into the bundle 10 of the sized glass filaments.

All the filaments of the bundle 10 and of the sheet 12 thus mingled are joined together by an assembling wheel 19 into a composite yarn 20.

This yarn 20 is wound, for example in the form of a straight-sided package 21, on the spindle 22 of a turret-type bobbin winder 23. The filaments of the sheet 12 are drawn by the drums 14, for example at a speed $V_1$ which is greater than the speed $V_2$ of the filaments of the bundle 10 which are drawn by the spindle 22. As was explained previously, this speed difference makes it possible to compensate for the shrinkage of the thermoplastic filaments which occurs before the composite yarn 20 is wound on the spindle 22. This speed difference is different depending on the nature of the thermoplastic organic substance used and/or on the chosen drawing conditions.

The venturi 18 projects the sheet 12 at a speed which is normally identical to $V_1$. As a result, the tension in the sheet 12, between the last mechanical members of the device 13 and the venturi 18, is very low and practically constant. This tension is so low that the sheet 12 forms a catenary under the effect of its own weight between the roller 16 and the roller 17. No conventional tension-control device is suitable for measuring such a low level of tension.

The device according to the invention comprises, in the embodiment illustrated in FIG. 1, four detectors $d_1$, $d_2$, $d_3$ and $d_4$ arranged at different heights which delimit a region through which the sheet 12 can move. These detectors are fixed to a support 24 placed between the rollers 16 and 17.

Each of these detectors comprises an emitter and a receiver which work together. Each emitter emits a light beam consisting of pulses. When this beam encounters the filaments of the sheet 12, some of the light is collected by the associated receiver. The information received by each receiver is converted separately by the amplifiers $a_1$, $a_2$, $a_3$, $a_4$ which send a binary signal to a controller. This controller has a control output (analogue or digital) which is connected to the external speed-setting input of a frequency converter for controlling the motors which drive the drums 14. The controller continuously analyses the logic state of the detectors and, by means of a program, regulates the speed of rotation of the drums 14 so as to keep the tension in the sheet 12 to a minimum value, as shown by the following example: when the sheet 12 is taut, only the detector $d_1$ detects its presence; the controller records this situation and speeds up the motors. If the sheet 12 then reaches the $d_2$ level, the controller speeds up the motors less than in the previous case. If the sheet reaches the $d_3$ level, the controller stabilizes the speed of the motors. If the sheet 12 slackens further, the detector $d_4$ records its presence and the controller slows down the motors, this having the effect of assuming a slight delay with respect to the winding speed of the yarn 20 and of retensioning the sheet 12. In order to avoid accelerations which are continually followed by decelerations and vice versa, the program governing the controller may comprise time constants and the accelerations and decelerations may be quantified.

The device according to the invention is preferably employed using a bobbin winder comprising several spindles, of the turret-type bobbin winder 23. This makes is possible to produce successive packages without interrupting the operations of drawing the glass filaments and the thermoplastic organic filaments.

The transfer operation is effected in a manner known per se: when the package 21 reaches the desired size, the yarn 20 is moved away towards the free end of the spindle 22 on which it is being wound, the spindle 22a being set into rotation, the turret 25 performs a half-rotation so that the said spindle takes the place of the spindle 22. The yarn 20 is then wound onto the free end of the spindle 22a before resuming its initial path in order to produce a new package.

This transfer is accompanied by sudden variations in the speed of the sheet 12 which are prejudicial to the proper operation of the installation.

A first embodiment, illustrated in FIGS. 2A, 2B, 2C, enables these variations to be considerably reduced.

FIG. 2A shows a drawing device 26 provided with three motor-driven drums 27, 28 and 29 which entrain the sheet of thermoplastic filaments 30.

FIG. 2B shows the drawing device 26 as well as the drums 27 and 28 on which the sheet of filaments 30 is in a drawing position. These drums are provided on their free end with idlers 31 and 32. The drum 29, not shown, is also equipped with an idler.

Right from the start of the transfer operation, the sheet 30 is brought into contact with the idlers, as shown in FIG. 2C. This operation may result either from a lateral shift of the sheet 30, by means of a device not shown, or a lateral shift of the entire device 26 mounted on slideways, not shown. The sheet 30 is then only entrained by filaments 10 which are being drawn.

The controller, connected via a circuit to the bobbin winder 23, receives the information regarding the start and finish of the transfer operation. The signal corresponding to the start of the operation has the effect of switching off the detectors which detect the presence of the sheet and of giving the motors driving the drums a rotation speed setting which is less than the normal drawing speed. The signal corresponding to the finish of the transfer operation has the effect of turning the detectors back on and of increasing the speed of rotation of the drums to the normal drawing speed.

A second embodiment of the device according to the invention also makes it possible to reduce the sudden variations in speed during the transfer operation. This second embodiment is illustrated in FIGS. 3A and 3B.

FIG. 3A shows a drawing device 33 provided with five motor-driven drums 34, 35, 36, 37 and 38 which entrain the sheet of thermoplastic filaments 39. In this device, when operating, the drums 34, 36 and 38 in the high position are arranged alternately with the drums 35 and 37 in the low position, the device 40 for detecting the sheet being in operation.

FIG. 3B shows the same device during the transfer operation.

The signal corresponding to the start of the operation, sent to the controller, has the effect of moving the drums 35 and 37 vertically along slideways 41 and 42. At the end of this vertical movement, the sheet 39 is released and only touches the upper part of the drums 34, 36 and 38. The signal corresponding to the finish of the transfer operation has the effect of returning the drums to their initial positions. As previously, these signals have the effect of switching off and then turning back on the detection device 40 and of giving the motors driving the drums various speeds of rotation.

A third embodiment of the device according to the invention enables the sudden variations in speed during the transfer operation to be reduced. This third embodiment is illustrated by FIGS. 4A, 4B and 4C.

FIG. 4A shows a drawing device 43 provided with two motor-driven drums 44 and 45 mounted on a turret 46. This figure shows this device in the normal drawing position. A guide roller 47 is placed upstream of the device 43 in order to increase the arc of contact of the sheet of filaments 48 with the drum 44. Downstream, the detection device 49 is operating.

FIG. 4B shows the device 43 during the transfer operation.

The signal corresponding to the start of the operation, sent to the controller, has the effect of rotating the turret 46 so as to release the sheet 48 completely. The signal corresponding to the finish of the transfer operation has the effect of rotating the turret 46 in the opposite direction so as to reestablish the drums 44 and 45 in their initial positions.

In a variant, it is possible to give the turret 46 a more limited rotation of the sheet with the drums 44 and 45. This variant has the advantage of reducing the tension induced in the sheet 48 and makes it possible to use a series of drawing devices, as shown in FIG. 4C.

The installation shown in this figure has three devices 50, 51 and 52 mounted in series. Each of these devices comprises two motor-driven drums 53, each pair of drums being mounted on a turret 54. FIG. 4C shows the installation in the normal drawing position with a guide roller 55 upstream of the device 50 and a detection device 56 downstream of the device 53.

The operation of the previous devices, described in the case of an operation of transferring the composite yarn from one spindle to another, is the same when it is a question of starting the drawing of the organic filaments or of restarting their drawing if it has been interrupted for one reason or another.

One or more drums of the drawing devices may be provided with heating elements capable of raising their surface to a defined temperature, it being possible for these elements to be controlled individually, so as to be able to regulate the temperature, to which the surface of each drum will be raised, separately. The heat treatment undergone by the sheet of filaments during its contact with the surface of the said drums makes it possible to stabilize, at least partly, the structural modification of the polymer which has arisen when drawing it into the form of filaments. In this embodiment, the drawing speed given to the thermoplastic organic filaments may be barely greater, or indeed equal to that of the glass filaments with which they are combined.

Although the shrinkage phenomenon occurring in the thermoplastic organic filaments is reduced, or even eliminated, because of this heat treatment, the device for detecting the sheet retains all its advantage since its essential function is to keep its tension at the lowest and most constant value possible, whatever the drawing speed of the said sheet.

What is claimed is:

1. Device for manufacturing a composite yarn formed by the composition of continuous glass filaments and continuous filaments of a thermoplastic organic substance, comprising;
   at least one bushing which is fed with glass, the lower face of said bushing being provided with a multiplicity of orifices from which a multiplicity of glass filaments may be drawn;
   a coating device positioned to coat glass filaments from said bushing;
   at least one extrusion head capable of being fed with a molten thermoplastic organic substance, the lower face of said extrusion head being provided with a multiplicity of orifices from which a multiplicity of organic filaments may be drawn, said head being associated with a drawing device comprising at least two drums and a venturi device which projects organic filaments from the extrusion head into a sheet formed by the glass filaments to form a composite yarn;
   a composite yarn forming device;
   an optical yarn detecting device arranged between the drawing device and the venturi device; and
   a circuit which controls the speed of rotation of at least one of the drums based on information from said yarn detecting device.

2. Device according to claim 1, wherein the yarn detecting device comprises at least 2 detectors placed on support at different heights which define the limits of a region in which the said sheet can move during the operation of drawing the thermoplastic filaments.

3. Device according to claim 2, wherein the detectors are arranged on only one side of the sheet and are each provided with an emitter capable of emitting a light beam and with a receiver capable of receiving at least some of the light reflected by the thermoplastic filaments which encounter the said beam.

4. Device according to claim 3, wherein the emitters emit a light beam having regular pulses.

5. Device according to claim 4, characterized in that the receivers of the detectors are connected, via an amplifier, to a controller whose output is connected to the control device for the motor or motors controlling the speed of rotation of the drums.

6. Device according to claim 3, wherein the receivers of the detectors are connected, via an amplifier, to a controller whose output is connected via an amplifier, to the control device for a motor controlling the speed of rotation of the drums.

7. Device according to claim 6, wherein the controller is connected to the winding device via a circuit which transmits to the winding device information regarding the start and finish of the operation of transferring the composite yarn and of the operation of restarting the drawing of the thermoplastic filaments.

8. device according to claim 7, wherein the controller is governed by a program which controls the switching off of the detection device, a variation in the speed of rotation of the drums and any shift of the said drums at the start and finish of the operation of transferring the composite yarn or of the operation of restarting the drawing of the thermoplastic filaments.

9. Device according to claim 8, wherein the free end of the drums of the drawing device includes an idler mounted on the shaft of each of the said drums.

10. Device according to claim 9, wherein the drawing device is moveable and capable of moving laterally closer to and away from the path followed by the sheet of thermoplastic filaments.

11. Device according to claim 10, wherein during the operation of transferring the composite yarn or during the operation of restarting the drawing of the thermoplastic filaments, the said device moves away until the sheet of thermoplastic filaments comes into contact with the idlers and then resumes its initial position after the said restart or the said transfer.

12. Device according to claim 9, wherein one or more of the drums of the drawing device are capable of being heated so as to stabilize the structure of the thermoplastic filaments.

13. Device according to claim 12, wherein the drawing device comprises several drums provided with a heating means, each of the means being capable of being controlled individually so as to regulate the temperature, to which the surface of each drum will be raised, separately.

14. Device according to claim 8, wherein the drums of the drawing device are mounted on at least one turret capable of rotating about an axis parallel to the axis of rotation of the said drums.

15. Device according to claim 14, wherein, during the transfer or restart operation, the turret rotates so as to move the drums away from the sheet of thermoplastic filaments at the start of the said operation, resuming its initial position after the said operation.

16. Device according to claim 8, wherein the drums of the drawing device are mounted on a fixed stand, at least one of the drums being capable of moving perpendicularly to the sheet of thermoplastic filaments.

17. Device according to claim 16, wherein, during the transfer or restart operation, at least one of the drums moves away from the sheet of thermoplastic filaments at the start of the operation and then resumes its initial position after the said operation.

18. Device according to claim 2, wherein the detectors consist of emitters and of receivers which are arranged on each side of the sheet of thermoplastic filaments and act together in pairs.

19. Device according to claim 18, characterized in that the emitters emit a light beam consisting of regular pulses.

20. Device according to claim 18, characterized in that the receivers of the detectors are connected, via an amplifier, to a controller whose output is connected to the control device for the motor or motors controlling the speed of rotation of the drums.

\* \* \* \* \*